(12) United States Patent
Riebel et al.

(10) Patent No.: US 7,767,144 B2
(45) Date of Patent: Aug. 3, 2010

(54) RAPID DIAGNOSIS DEVICE WITH LOCKING BY TEST STRIP

(75) Inventors: Stefan Riebel, Mannheim (DE); Manfred Augstein, Mannheim (DE); Rainer Stöhar, Föritz (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1061 days.

(21) Appl. No.: 11/003,162

(22) Filed: Dec. 3, 2004

(65) Prior Publication Data

US 2005/0129574 A1    Jun. 16, 2005

(30) Foreign Application Priority Data

Dec. 3, 2003    (DE) ................................ 103 56 452

(51) Int. Cl.
*G01N 33/00* (2006.01)
(52) U.S. Cl. ............................. 422/58; 422/99; 422/102
(58) Field of Classification Search .................. 422/58, 422/99, 102
See application file for complete search history.

(56) References Cited

U.S. PATENT DOCUMENTS

| 3,780,283 | A | | 12/1973 | Poweska et al. |
| 5,281,395 | A | | 1/1994 | Markart et al. |
| 5,304,468 | A | * | 4/1994 | Phillips et al. ................ 435/14 |
| 5,515,170 | A | | 5/1996 | Matzinger et al. |
| 5,872,713 | A | * | 2/1999 | Douglas et al. ............... 702/85 |
| 6,506,168 | B1 | * | 1/2003 | Fathallah et al. ............ 600/578 |

FOREIGN PATENT DOCUMENTS

WO    WO 02/094092 A1    11/2002

* cited by examiner

*Primary Examiner*—Sam P Siefke
(74) *Attorney, Agent, or Firm*—Dinsmore & Shohl LLP

(57) ABSTRACT

The invention relates to a rapid diagnosis device with a device housing, on which there is provided a push-in opening for a test strip. The test strip is evaluated inside the rapid diagnosis device. On the device housing there is formed a housing opening, which can be closed by a cover or flap element. The cover or flap element is assigned a locking body. The locking body is formed as a spring element which comprises a clip portion, which assumes a position locking the spring element when the test strip has been pushed into the push-in opening of the rapid diagnosis device.

12 Claims, 3 Drawing Sheets

RAPID DIAGNOSIS DEVICE WITH LOCKING BY TEST STRIP

BACKGROUND OF THE INVENTION

The present invention relates to a rapid diagnosis device with locking of a cover element, in particular when a test strip has been inserted into the rapid diagnosis device, the rapid diagnosis device having a heating element and being exposed to environmental influences.

In the case of rapid diagnosis devices of the kind commonly used today for the evaluation of test strips, soiling of a heating element used in the rapid diagnosis device occurs after it has been in operation for quite a long time. The arrangement of the heating element is required to bring the test strip to a specific temperature, permitting optimum evaluation of the specimen being measured. In the course of time, particles are deposited on the heating element which is accommodated inside the device housing of the rapid diagnosis device and they have to be removed from time to time, since, when there is an increasing build-up of particles on the heating element, its efficiency is impaired or the current consumption of the heating element becomes too great. In order to clean from time to time the heating element accommodated inside the device housing of the rapid diagnosis device, the removal of a cover element or a flap element which is let into the device housing is required. Therefore, the device housing is provided with a sheet-like element which is generally designed as a cover or as a flap and can be removed from the device housing. The removable sheet-like element also allows disturbing ambient light to enter the interior of the device housing, which can impair the measurement considerably, in particular in the case of optical measuring devices with which test elements or test strips are evaluated by optical means.

In general, a housing opening which can be closed by the cover or a flap element lies on the side of the device housing of the rapid diagnosis device in which the push-in opening for a test strip to be pushed into the interior of the device housing lies.

It has been found that, when the test strip to be evaluated inside the rapid diagnosis device is pushed in, there are isolated instances in which the cover or the flap closing the device housing is inadvertently or intentionally opened, which can lead to erroneous measurements, i.e., defective evaluations of the test strip pushed into the interior of the housing.

The erroneous measurements are attributable to the fact that a sudden temperature change can occur in the ambience of the test strip to be evaluated on account of the removal of the cover or opening of the flap on the front side of the device housing of the rapid diagnosis device. The missing cover element or the missing flap element at the housing opening allows entry of ambient air, which considerably influences the temperature level produced by the heating element in the interior of the device housing, so that a test strip evaluated under changing ambient conditions with regard to the temperature may lead to an unusable test result. With a missing cover element, it is also possible in particular in the case of optical measuring devices for disturbing ambient light to enter the interior of the device housing, which considerably impairs the evaluation of test elements to be evaluated optically.

Apart from a defective measurement, abnormal termination of the measurement may also occur.

SUMMARY OF THE INVENTION

It is against the above background that the present invention provides certain unobvious advantages and advancements over the prior art. In particular, the inventor has recognized a need for improvements in rapid diagnosis device design.

Although the present invention is not limited to specific advantages or functionality, it is noted that the present invention provides protection of the rapid diagnosis device during the evaluation of a test strip against inadvertent or unintentional opening and keeps disturbing environment influences away from the interior of the device.

In accordance with one embodiment of the present invention, a rapid diagnosis device comprising a device housing is provided, wherein the device housing comprises a push-in opening for a test strip and a housing opening, and wherein the test strip is evaluated inside the rapid diagnosis device, and the housing opening can be closed by a cover or flap element. The cover or flap element is assigned a locking body. The locking body is configured as a spring element which comprises a clip portion. The clip portion is configured to lock the spring element when the test strip is pushed into the push-in opening.

In accordance with the several embodiments of the present invention, a rapid diagnosis device is provided of which the housing is protected against unintentional opening during a measuring operation. Used for this purpose according to the instant invention is the test strip that can pushed into the push-in opening for the evaluation, which deflects a clip part of a spring element in such a way that an unlocking of the cover element for opening the cover or flap element on the housing is blocked. The locking proposed according to the embodiment of the present invention by the test strip that is pushed into a push-in opening and is to be measured inside the rapid diagnosis device takes place by using a spring element which is clipped in on the underside of the cover or flap element closing the housing opening.

The spring element which can be clipped in on the underside of the cover or flap element advantageously comprises a clip portion, which merges into a spring tongue, and also two spring legs. Peg elements with the aid of which the spring element can be clipped into corresponding receiving openings on the underside of the cover or flap element may be formed on the spring legs in the region of stops. The spring element may alternatively also be seated in the device housing.

The clip element, which extends essentially between the two legs of the spring element, may be of a cranked form and have on its sides facing towards the test strip bearing webs with which the pushing-in movement of the test strip into the housing interior of the rapid diagnosis device can be assisted.

In accordance with the several embodiments of the present invention, the invention achieves the effect that, when a test strip is inserted in a receiving slot, the clip portion lying between the two spring legs is deflected in such a way that a lateral unlocking movement of the stops on the two mutually parallel running spring legs of the spring element on the underside of the cover or flap element is blocked. If, on the other hand, the test strip has not been inserted into the insertion slot, the clip portion arranged between the two spring legs protrudes into the region in which the test strip is otherwise inserted. On account of this, the two stops which are arranged lying opposite each other on the two spring legs do not bear against the clip portion and are able to perform a lateral unlocking movement, so that the cover element can be removed from the housing opening of the housing body of the rapid diagnosis measuring device.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF TYPICAL EMBODIMENTS OF THE INVENTION

Figure 1:
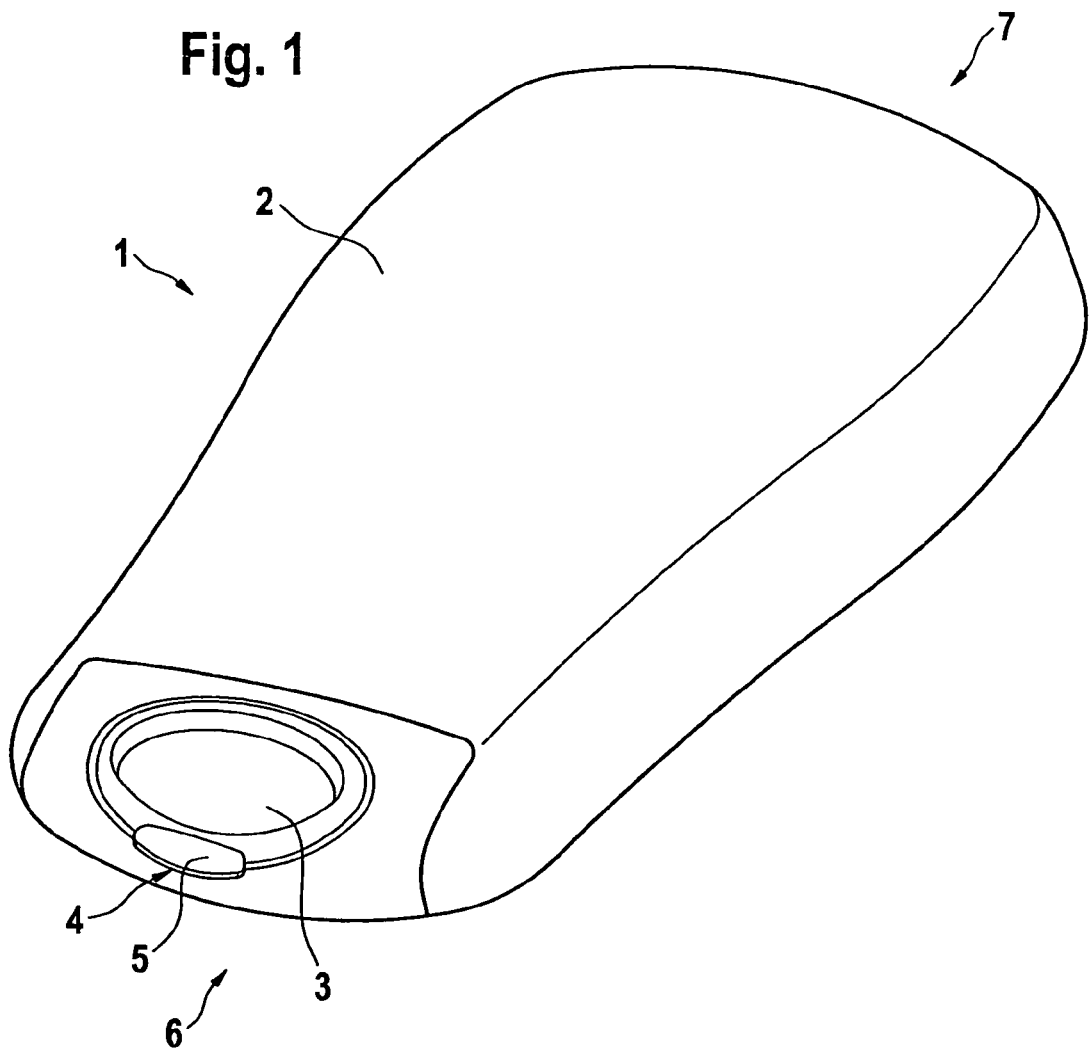
FIG. 1 shows a plan view of a device housing of a rapid diagnosis device in accordance with an embodiment of the present invention.

Referring initially to FIG. 1, in accordance with one embodiment of the present invention, a rapid diagnosis device 1 is shown which comprises a device housing 2. A device housing opening, formed in the device housing 2, is closed by a cover or flap element 3. Underneath the cover or flap element 3 there is a slot-shaped push-in opening 4, in which a test strip to be evaluated inside the rapid diagnosis device 1 can be pushed in. The push-in opening 4 for the test strip is bounded on the one hand by a portion of the cover or flap element 3 or on the other hand by a flat-formed push-in tongue 5. The push-in opening 4 for the test strip to be pushed into the device housing 2 is located on a front side 6 of the device housing 2, the rear side of which is identified by reference numeral 7. The push-in opening 4, which according to the configurational variant of the rapid diagnosis device 1 according to FIG. 1 is formed on its front side 6, could also be formed equally well on its rear side 7.

Figure 2:
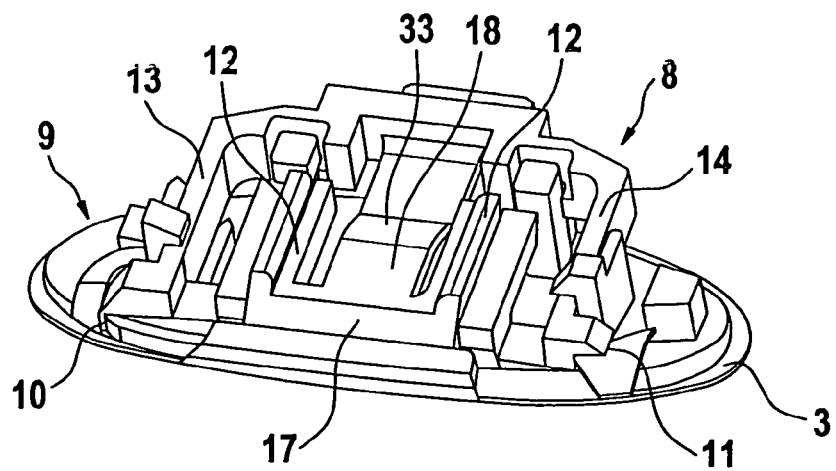
FIG. 2 shows the underside of a cover element, closing a device housing opening, with a locking body in accordance with an embodiment of the present invention.

In accordance with another embodiment of the present invention, FIG. 2 shows the underside of a cover or flap element 3 closing the housing opening, with a locking body attached to it. The locking body formed as a locking body 8 is accommodated on an underside 9 of the cover or flap element 3. Alternatively, this locking body may also be seated in the device housing 2. A first spring leg 13 and a second spring leg 14 are formed on the locking body 8, which is formed as a spring element. The two spring legs 13 and 14 extend parallel to a spring tongue 18, at the end of which a clip portion 17 is formed. The spring tongue 18 may be provided with a crank 33. In the region protruding upwards through the crank 33 of the spring element 8 that is represented in FIG. 2 and serves as a locking body, one or more bearing webs 12 are typically formed for the contacting of the test strip.

Figure 4:
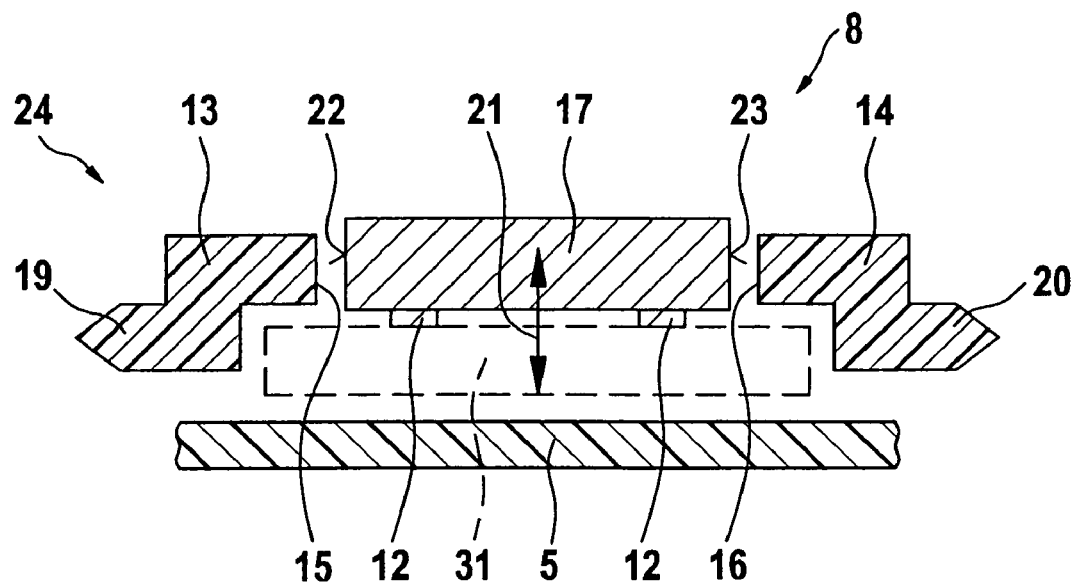
FIG. 4 shows a clip portion of the locking body in a locking position brought about by an inserted test strip in accordance with an embodiment of the present invention.
Figure 5:
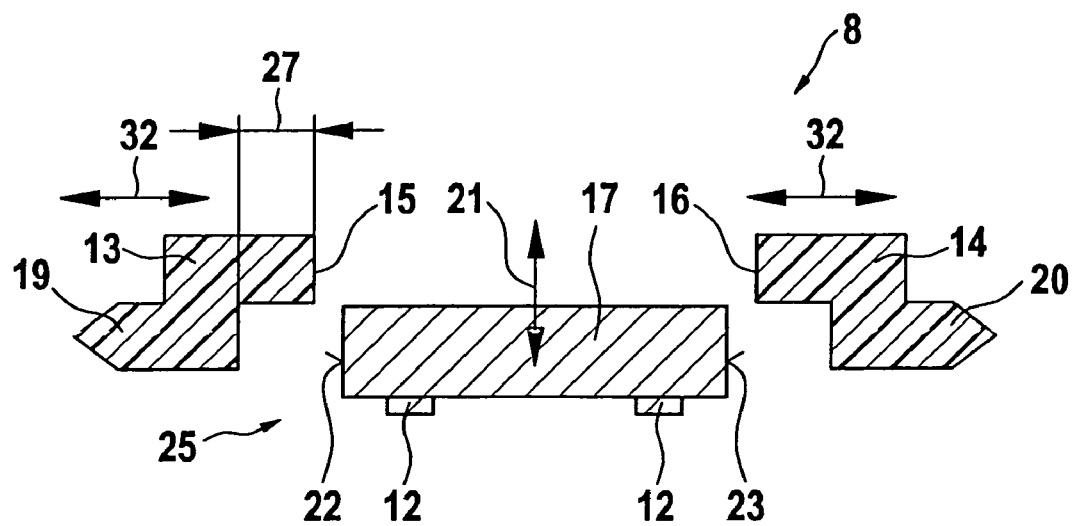
FIG. 5 shows the clip portion of the locking body in a position permitting an unlocking cover or flap element in accordance with an embodiment of the present invention.

Pegs 19 and 20 may be arranged on the two spring legs 13 and 14, respectively, of the spring element 8 serving as a locking body (compare the embodiments represented in FIGS. 4 and 5). The locking body 8 used as a locking body is typically produced as a plastic injection-molded component according to a one-component or multi-component injection-molding process, whereby it can be formed in one piece and it is possible to injection-mold in one operation not only the spring tongue 18 that is provided with a crank 33 but also the bearing webs 12 formed therein, the first spring leg 13 and the second spring leg 14 and pegs 19 and 20 typically molded onto the latter.

The pegs 19 and 20, represented in FIGS. 4 and 5, are clipped into a first clip-in location 10 and also a second clip-in location 11 on the cover underside 9 of the cover or flap element 3.

The locking body 8, which is represented in FIG. 2 and serves as a locking body, is shown from its underside, with which it lies opposite a test strip pushed into the push-in opening 4 according to FIG. 1.

Figure 3:
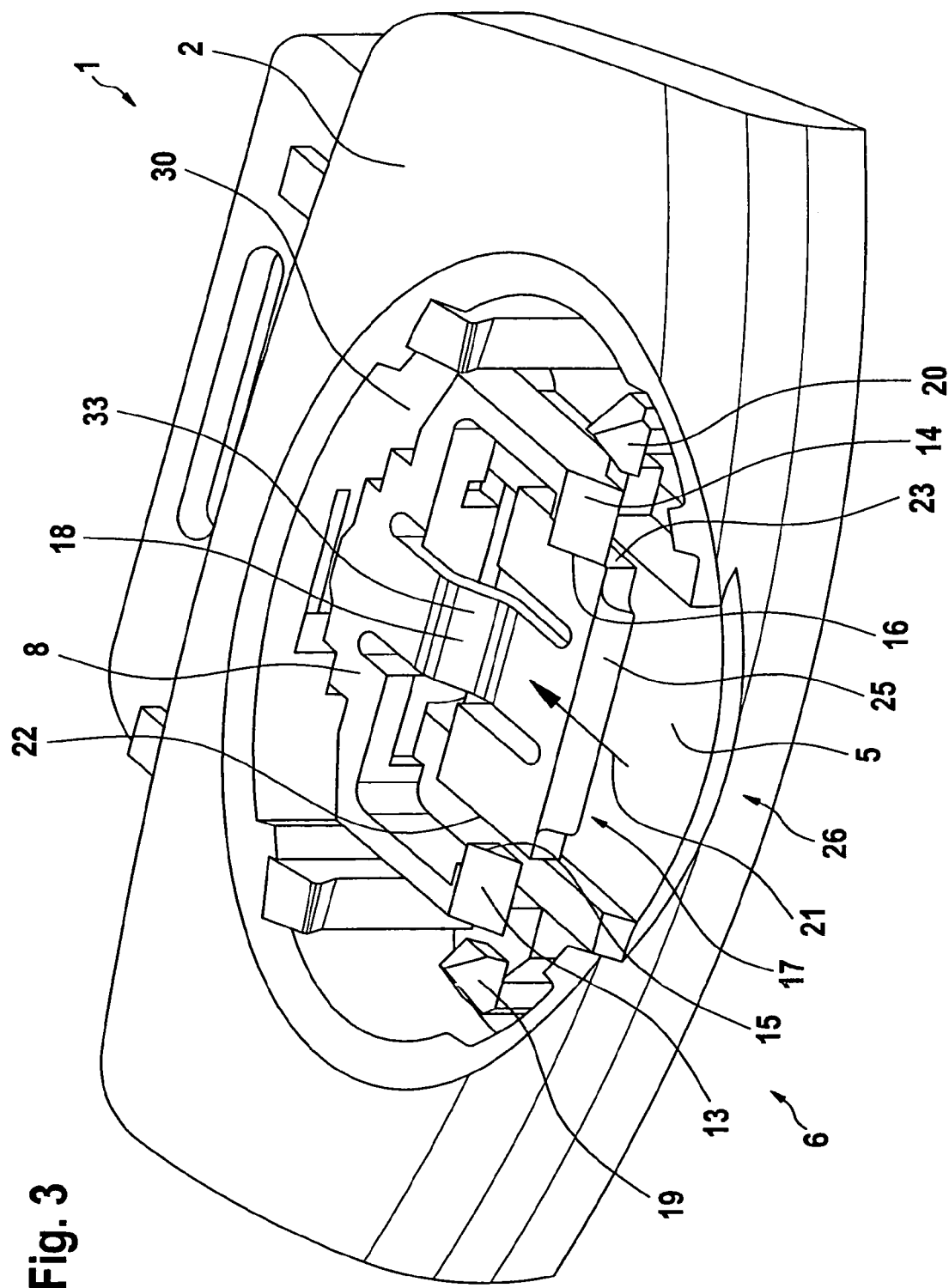
FIG. 3 shows a reproduction, represented on an enlarged scale, of the front edge of the device housing with the device housing opening exposed in accordance with an embodiment of the present invention.

The embodiment of the present invention represented in FIG. 3 reveals the exposed housing opening at the front edge of the device housing of the rapid diagnosis device on an enlarged scale.

Formed on the front side 6 of the device housing 2 of the rapid diagnosis device 1 is an oval-formed housing opening 30. The underside of the housing opening 30 is formed by the push-in tongue 5 for a test strip, which is not represented in FIG. 3. Above the insertion tongue 5, the clip portion 17 of the spring tongue 18 is located in a second clip portion position 25, in which a release of the cover or flap element 3 removed from the housing opening 30 is made possible. The embodiment represented in FIG. 3 reveals that the spring tongue 18, the front end of which is formed by the clip portion 17, has a crank 33. The crank 33 of the spring tongue 18 improves the resilient property of the spring tongue 18 and the bearing webs 12 formed on it (compare the embodiment represented in FIG. 2) against the test strip to be pushed into the push-in opening 4. Stops 15, 16 are respectively formed on spring legs 13 and 14 extending on both sides of the spring tongue 18. The stops 15, 16 face towards side faces 22, 23 of the spring tongue 18, which are deflected in the direction of movement indicated by the arrow 21 as soon as a test strip is pushed into the push-in opening 4.

In the second clip position 25, represented in FIG. 3, of the clip portion 17 of the spring tongue 18, the clip portion 17 lies below the mutually facing stops 15, 16 of the spring legs 13 and 14. This permits their lateral deflection (compare the embodiment represented in FIG. 5) for unlocking the cover or flap element 3 for removal of the latter from the housing opening 30.

Molded onto the outer sides of the spring legs 13 and 14, arranged parallel to each other, there is respectively a first peg 19 and a second peg 20, with which the locking body 8 serving as a locking body can be clipped into corresponding clip-in locations 10, 11 on the underside 9 of the cover or flap element (compare the embodiment represented in FIG. 2).

In accordance with still another embodiment of the present invention, FIG. 4 shows a clip portion of the spring element deflected by a test strip. FIG. 4 reveals that a test strip 31 has been pushed into the push-in opening 4 in the lower region of the housing opening 30 at the front side 6 of the device housing 2. When the test strip 31 is pushed in, it rests with its underside on the push-in tongue 5 (compare the embodiment represented in FIG. 3). The upper side of the test strip 31 contacts the bearing webs 12 formed on the underside of the spring tongue 18 (compare the embodiment according to FIG. 2). When the test strip 31 is pushed in completely along the push-in tongue 5, the spring tongue 18 is deflected with its clip portion 17 formed on it into the first clip position 24, represented in FIG. 4. In the first clip position 24, which forms the locking position of the cover or flap element, not represented in FIG. 4, in the housing opening 30, the first side face 22 of the spring tongue 18 lies opposite the first stop 15. At the same time, the second side face 23 of the spring tongue 18 lies opposite the second stop 16. The clip portion 17 of the spring tongue 18 blocks a lateral deflection of the spring legs 13 and 14 in the first clip position 24, represented in FIG. 4, so that an unlocking of the cover element 3, i.e., its removal from the housing opening 30 represented in FIG. 3, whether intentionally or inadvertently, is no longer possible when the test strip 31 has been pushed into the push-in tongue 5. As a result, it is prevented that a measuring operation in progress with a pushed-in measuring strip 31 inside the rapid diagnosis device 1 is abnormally terminated or erroneous measurements occur because the housing opening 30 is opened during the measuring operation and the temperature inside the device housing 3 changes abruptly during the measuring operation.

In the embodiment of the present invention represented in FIG. 4, a first peg 19 and a second peg 20 are respectively molded onto the outer sides of the spring legs 13 and 14. With reference to the stops 15 and 16, formed on the inner side of the spring legs 13, 14, facing towards the spring tongue 18, the first peg 19 and the second peg 20 lie on the outer side of the spring legs 13 and 14, offset with respect to the first stop 15 and with respect to the second stop 16. The spring legs 13 and 14 of the spring element 8 which acts as a locking body run perpendicularly in relation to the plane of the drawing in the embodiment represented in FIG. 4. Reference numeral 21 identifies the direction of movement of the clip portion 17, i.e., of the front side of the spring tongue 18 of the spring element 8, which is movable between the first spring leg 13 and the second spring leg 14 in a freely movable manner corresponding to its elasticity. The force with which the spring tongue 18 is made to act against the test strip 31 to be pushed into the push-in opening 4 can be determined by the degree of the crank 33, in which the first spring tongue 18 can be formed (compare the embodiment represented in FIG. 3).

In accordance with yet another embodiment of the present invention represented in FIG. 5, the spring element serving as a locking body is represented in its second clip position, i.e., in a position permitting the release of the cover or flap element.

If there is no test strip 31 in the push-in opening 4 of the device housing 2 according to the embodiment of the present invention represented in FIG. 1, on the push-in tongue 5, there is no force deflecting the spring tongue 18, the clip portion 17 of which is represented in FIG. 5, in the direction of movement 21. The bearing webs 12 on the side facing towards the test strip of the spring tongue 18 or of the optionally cranked spring tongue 18 and of the spring portion 17 remain in a position above the push-in tongue 5. Since the clip portion 17 of the optionally cranked spring tongue 18 of the spring element 8 is not deflected in the direction of movement 21, the said clip portion does not move with its side faces 22, 23 in between the first stop 15 and the second stop 16. Therefore, the first spring leg 13 and the second spring leg 14 can perform a deflection 32 in the lateral direction, indicated by the double arrow. The second clip position 25, represented in FIG. 5, corresponds to the second clip position 25 as it is also represented in FIG. 3.

The lateral deflecting movement of the stops of the spring legs 13 and 14 with the stops 15 and 16 formed on their inner side is identified by reference numeral 32. Formed on the outer side of the first spring leg 13 and of the second spring leg 14 are the first peg 19 and the second peg 20, which can disengage when there is a lateral deflection 32 of the spring legs 14 and 13 from their clip-in locations 10 and 11, respectively, on the underside 9 of the cover or flap element 3. To release the cover 3, the pegs 19, 20 move back out of their clip-in locations 10 and 11, respectively. Owing to the resilient force that is inherent in the locking body 8 formed as a spring element, the first and second pegs 19, 20 that are formed on the first spring leg 13 and on the second spring leg 14 rapidly return to their starting position. The locking body 8 serving as a locking body does not remain in the position represented in FIG. 3 after removal of the cover element 3 from the housing opening 30, but moves upwards with the said element.

The stops 15 and 16 on the inner sides of the first spring leg 13 and the second spring leg 14, respectively, of the spring element 8 serving as a locking body are formed with a projection 27. The sum of the projections 27 of the first and second stops 15 and 16 together with the width of the locking portion 17 at the front end of the spring tongue 18 correspond essentially to the width of the test strip 31 pushed in on the push-in tongue 5 in FIG. 4. To facilitate the pushing-in of the test strip 31 in the pushing-in direction 36, the projection 27 is made to be somewhat larger with respect to the first stop 15 and the second stop 16, respectively, so that easy pushing-in, which can be performed in one motion, of a test strip 31 into the push-in opening 4 at the front side 6 of the rapid diagnosis device 1 is possible.

The heating element used inside the rapid diagnosis device serves for controlling the temperature of the evaluation or test strip. By means of the cover element 3, the heating element is protected against soiling and the interior of the device housing is protected against entry of ambient air, which could impair the measurement of an evaluation or test strip that is to be kept at a controlled temperature. If the rapid diagnosis device is a device operating by a purely optical process, disturbing ambient light can be kept away from the device housing of the rapid diagnosis device during the measurement by the cover element 3. The locking proposed according to the invention by the test or evaluation strip 31 itself may also be formed as such in which the test strip evaluation takes place by electrochemical means. The corresponding contacts on the measuring device can be protected by a cover or flap element 3 used on such diagnosis devices.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A rapid diagnosis device for a test strip comprising:
a cover or flap element comprising an underside with clip-in locations;
a device housing comprising a push-in opening which receives the test strip such that the test strip is evaluated inside the rapid diagnosis device, and a housing opening which is reversibly closable by the cover or flap element; and
a locking body formed as a spring element comprising laterally deflectable spring legs and a spring tongue resiliently arranged between the spring legs, the spring tongue comprising a clip portion positionable in a first and second position,
wherein in the first position, the clip portion allows lateral deflection of the spring legs and reversible engagement of the locking body with the clip-in locations of the cover or flap element, and
wherein in the second position, the clip portion blocks lateral deflection of the spring legs and disengagement of the clip-in locations by the locking body, the clip portion so positioned by the test strip when received through the push-in opening.

2. The rapid diagnosis device of claim 1, wherein the spring tongue is formed with a crank.

3. The rapid diagnosis device of claim 1, wherein bearing webs run on a side of the spring tongue facing the test strip.

4. The rapid diagnosis device of claim 1, wherein stops lying opposite side faces of the clip portion are formed on the spring legs.

5. The rapid diagnosis devise of claim 4, wherein the clip portion is positioned between the stops when the test strip is received through the push-in opening thereby blocking deflection of the stops in the lateral direction and preventing unlocking of the cover or flap element.

6. The rapid diagnosis device of claim 4, wherein the clip portion is positioned to permit a deflection of the stops and unlocking of the cover or flap element when the test strip is not received through the push-in opening.

7. The rapid diagnosis device of claim 1, wherein pegs which can be inserted into the clip-in locations on the cover or flap element are arranged on the spring legs.

8. The rapid diagnosis device of claim 4, wherein the stops on the spring legs are formed with a projection.

9. The rapid diagnosis device of claim 7, wherein the pegs are positioned offset with respect to one another on the spring legs.

10. The rapid diagnosis device of claim 8, wherein the stops are positioned offset with respect to one another on the spring legs.

11. The rapid diagnosis device of claim 1, wherein the locking body is seated on the underside of the cover or flap element.

12. The rapid diagnosis device of claim 1, wherein the locking body is seated within the device housing.

* * * * *